US00PP37649P2

(12) United States Plant Patent
Hansen

(10) Patent No.: US PP37,649 P2
(45) Date of Patent: Aug. 25, 2026

(54) ***THALICTRUM* PLANT NAMED 'Cotton Ball'**

(50) Latin Name: ***Thalictrum* hybrid**
Varietal Denomination: Cotton Ball

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 19/729,051

(22) Filed: Feb. 25, 2026

(51) Int. Cl.
*A01H 5/02* (2018.01)
*A01H 6/72* (2018.01)

(52) U.S. Cl.
USPC ..... Plt./263.1

(58) Field of Classification Search
USPC ..... Plt./263.1
See application file for complete search history.

(56) References Cited

U.S. PATENT DOCUMENTS

PP31,920 P2 * 6/2020 Delabroye ..... A01H 6/00
Plt./263.1

* cited by examiner

*Primary Examiner* — Karen M Redden

(57) ABSTRACT

The new and distinct cultivar of ornamental Meadow Rue, *Thalictrum* plant named 'Cotton Ball' with tripinnately compound foliage of medium green, wispy white-colored flowers on dark stems in late spring that appear well above the foliage. The new plant is winter-hardy and useful for ornamental purposes.

2 Drawing Sheets

Latin botanical classification: *Thalictrum* hybrid.
Variety denomination: 'Cotton Ball'.

STATEMENT REGARDING PRIOR DISCLOSURES UNDER 37 CFR 1.77(B)(6)

The first offer for sale was made by Walters Gardens, Inc. on Apr. 28, 2025, to Medford Nursery'. On Dec. 1, 2025, the new plant was first advertised on a website managed by Walters Gardens, Inc. The plant was also listed in the "Walters Gardens 2025-2026 Catalog" published and released on Jun. 3, 2025. Walters Gardens, Inc. obtained the new plant and all information about the new plant directly from the inventor. No plants of *Thalictrum* 'Cotton Ball' have been sold in this country or anywhere in the world, nor has any disclosure of the new plant been made more than one year prior the filing date of this application and such sale or disclosure within one year was either derived directly or indirectly from the inventor and therefore a 35 U.S.C. § 102(b) exception.

BACKGROUND OF THE INVENTION

The present invention relates to the new and distinct cultivar of Meadow Rue, botanically known as *Thalictrum* 'Cotton Ball', and hereinafter referred to as the cultivar 'Cotton Ball' or the "new plant." The new plant was an intentional cross by the inventor at a wholesale perennial nursery in Zeeland, Michigan, USA on Jun. 21, 2019, between *T. aquilegiifolium* 'Nimbus White' (not patented) as the female or seed parent and the male or pollen parent is a selection of *T. polygamum* known only as 'A' (not patented). The seeds were harvested on Aug. 7, 2019, and the new plant was assigned the breeder code 19-1-2 later in the evaluation process at the same nursery.

*Thalictrum* 'Cotton Ball' has been asexually propagated first in 2022 at the same nursery in Zeeland, MI by sterile plant tissue culture. Plants of 'Cotton Ball' have been found to be stable and identical to the original selection in multiple generations of asexual propagation.

SUMMARY OF THE INVENTION

The following traits have been repeatedly observed and represent the characteristics of the new cultivar. These attributes in combination distinguish 'Cotton Ball' as a unique cultivar of *Thalictrum:*

1. Tripinnately compound foliage of medium green;
2. Wispy white-colored flowers well above the foliage;
3. Winter-hardy habit with dark stems.

The female parent differs in having a shorter habit, white flowers and foliage that is bluish-green in color. The male parent differs in having a taller habit and creamy-white flowers.

The nearest comparison cultivars known to the inventor are: 'Nimbus White' (not patented), 'Black Stockings' (not patented), and 'Ghent Ebony' U.S. Plant Pat. No. 31,920.

*Thalictrum* 'Nimbus White' (not patented) has a much shorter habit and the flowers are white and the seed heads are lavender-pink. 'Black Stockings' (not patented) has a taller habit with stems that are darker purple, and the flowers are deep purple. 'Ghent Ebony' has a more compact habit, darker grey-purple foliage, and white flowers.

BRIEF DESCRIPTION OF THE DRAWINGS

The photographs of the new plant demonstrate the unique traits and the overall appearance of *Thalictrum* 'Cotton Ball'. The colors are as accurate as reasonably possible with color reproductions. Variation in ambient light spectrum, source and direction may cause the appearance of minor variation in color. The plant used in the photographs was a two-year-old plant and was grown in a full-sun nursery trial garden in Zeeland, Michigan with supplemental water and fertilizer when needed. No pinching or plant growth regulators have been used.

DETAILED BOTANICAL DESCRIPTION

Figure 1:
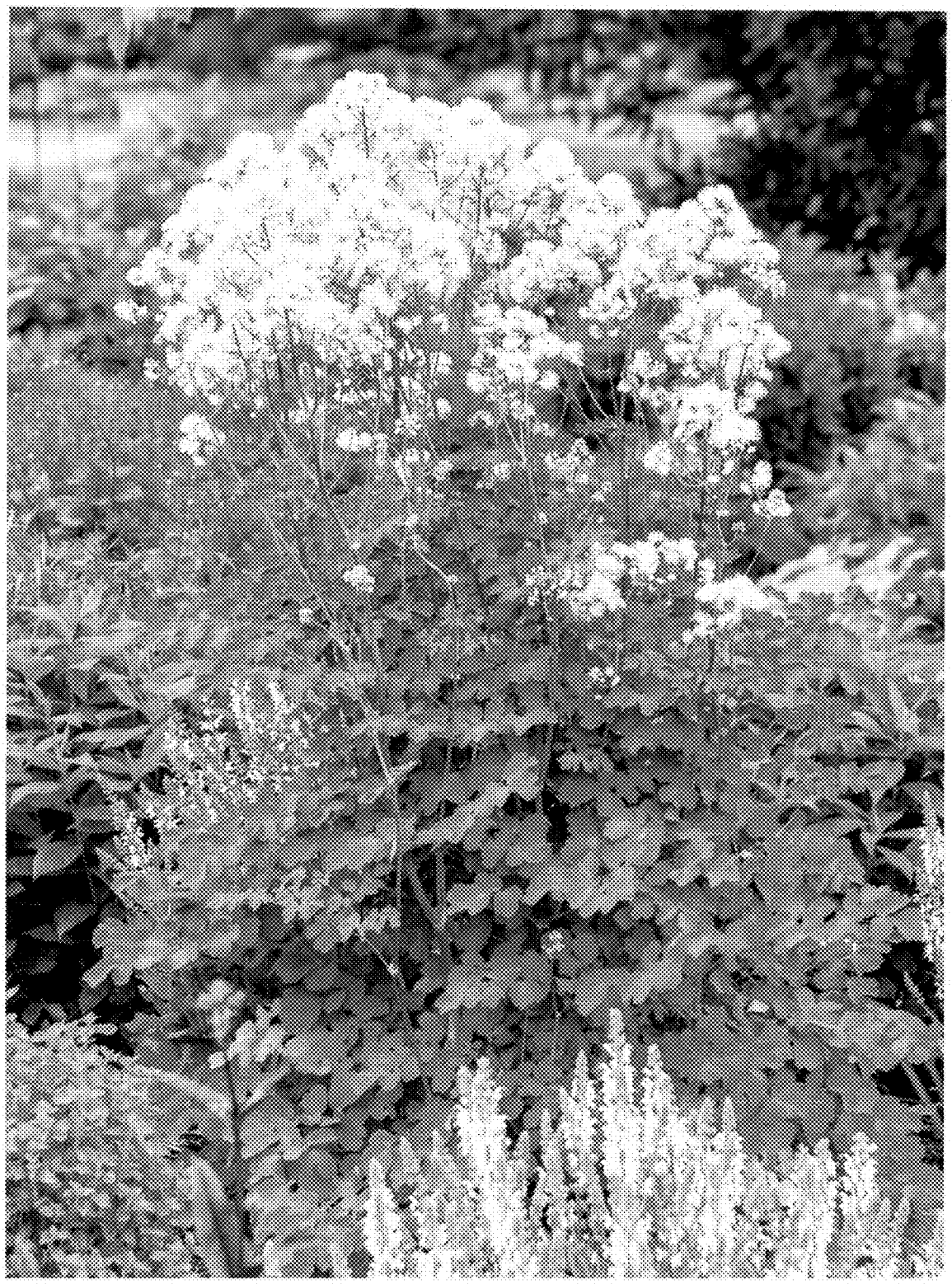
FIG. 1 shows the new plant in mid-season flowering habit.
Figure 2:
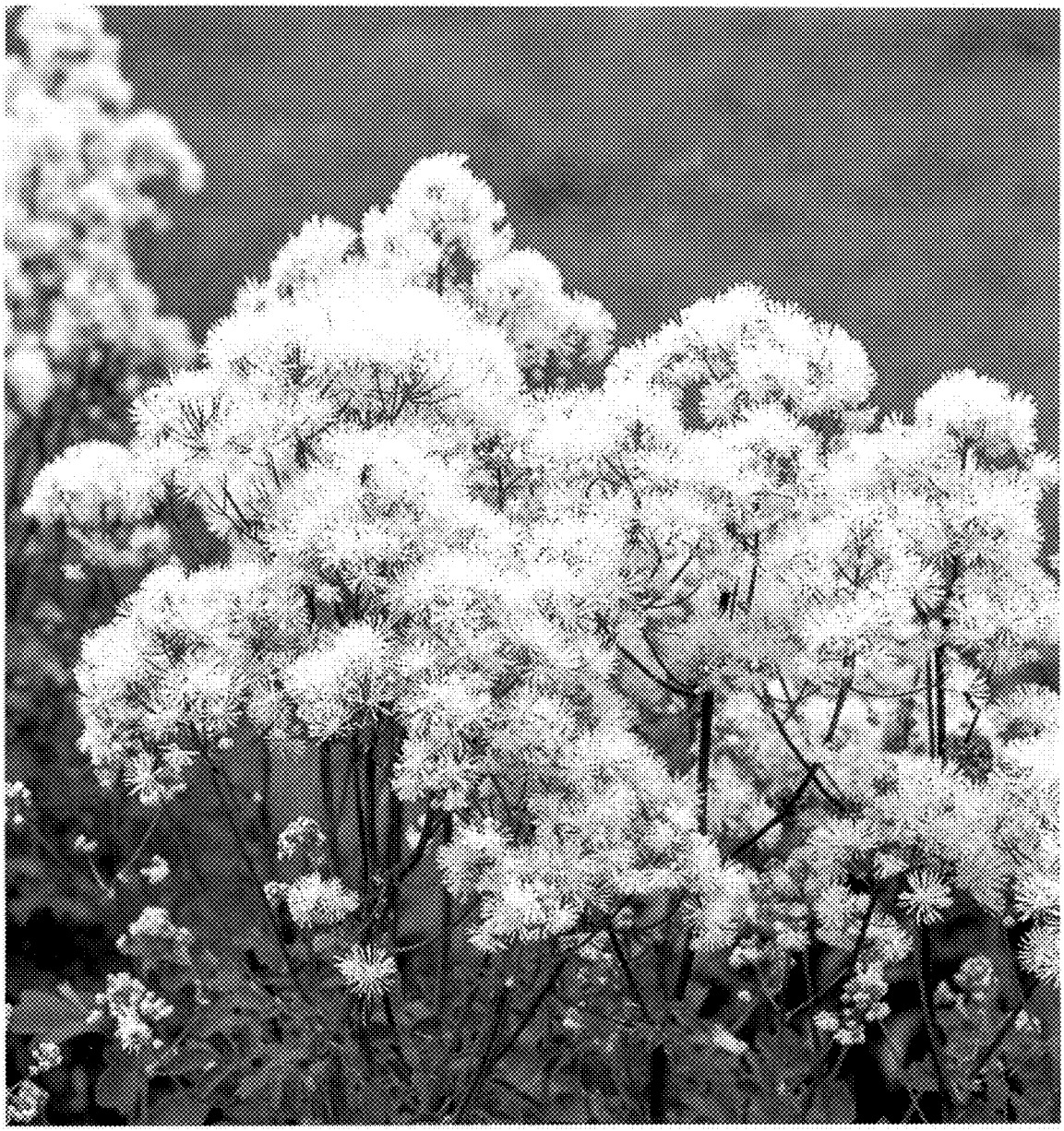
FIG. 2 shows a close-up of the flowers and buds.

The following descriptions and color references are based on the 2015 edition of The Royal Horticultural Society Colour Chart except where common dictionary terms are used. *Thalictrum* 'Cotton Ball' has not been observed under all possible environments. The phenotype may vary slightly with different growing environments such as temperature, light, fertility, soil pH, moisture and plant maturity levels, but without any change in the genotype. The following observations and size descriptions are based on three-year-old plants growing in a full-sun trial garden in Zeeland, MI. Plants were given supplemental water and fertilizer but no plant growth regulators were used.

Botanical classification: *Thalictrum* hybrid;

Parentage: Female or seed parent is *Thalictrum aquilegiifolium* 'Nimbus White'; male or pollen parent is *T. polygamum* 'A';

Plant habit: Winter-hardy herbaceous perennial with mounded foliage and about 8 upright flowering stems extending well above the plant; foliage to about 70 cm wide and 85 cm tall, flowering scapes to about 120 cm tall;

Growth rate: Moderately vigorous, finishing in a 3.8-liter container in about 11 weeks;

Root: Fibrous; developing to about 2 mm diameter; heavily branched; color nearest RHS 158D;

Stem: About 8 per plant; terete; fistulous; glabrous; slightly glaucous; lightly ribbed longitudinally; strength moderate; branching from base; to about 144 cm tall and 10 mm diameter at base;

Stem color: Variable, in regions of lower direct sunlight nearest RHS 146D and in regions of higher direct sunlight nearest RHS N77A;

Nodes: 8 below terminal inflorescence; average internode about 12.5 cm;

Node color: In low sunlight exposure nearest RHS 146D and in high direct sunlight nearest RHS N77A;

Foliage: Alternate; tripinnately compound; petiolate; broadly ovate to deltoid; basal foliage size up to 32 cm long and 37 cm wide, decreasing distally;

*Pinna*.—Oddly compound; overall deltoid.

*Pinnula*.—Typically 3 to 7 per rachilla; obovate; retuse to emarginate or rounded apex; base cordate to rounded; adaxial and abaxial surfaces glabrous, smooth, and matte; with 3 shallowly dissected broadly acute lobes and 3 to 7 variably dissected lobes from 2 mm to 12 mm deep forming lobes to about 9 mm long and 12 mm wide; variably dissected lobes dissected 3 to 15 mm deep, typically to ⅓ of the way to rarely all the way to the petiolule, forming lobes to 20 mm long and 12 mm wide; margins of leaflet entire; to about 40 mm long and 38 mm wide.

*Leaflet color*.—Young emerging nearest 138A adaxial and between RHS 138C and RHS 138B abaxial; adaxial maturing to between RHS 137C and RHS 137B, and abaxial between RHS 138C and RHS 138B.

*Leaflet fragrance*.—None detected.

*Venation*.—Palmate; glabrous and matte adaxial and abaxial; slightly costate abaxial smooth adaxial.

*Vein color*.—Adaxial nearest RHS 146D, abaxial nearest RHS 146C.

*Petiolules*.—Cylindrical; glabrous; slightly lustrous; to about 6.2 cm long and 3 mm across at base.

*Rachis*.—Cylindrical; fistulous; glabrous; slightly lustrous; to about 21.5 cm long and 5 mm diameter at base above stipules.

*Rachis color*.—Nearest RHS N77A dorsally, ventrally nearest RHS 146D.

*Rachilla*.—Cylindrical; fistulous; glabrous; slightly lustrous; to about 12 cm long and 1 to 1.5 mm diameter.

*Rachilla color*.—Dorsally a blend of RHS N77A and RHS 146C, ventrally nearest RHS 146D.

*Petioles*.—Cylindrical; fistulous; glabrous; slightly lustrous; clasping base; to about 12 cm long and 4 mm diameter at base before expanding to clasping portion of about 13 mm wide.

Petioles color: Ventrally between RHS 146D and RHS 145C, dorsally nearest RHS N77A;

Petiolule color: Ventrally nearest RHS 146D, dorsally nearest RHS N77A;

Stipules: At each node of stem and rachis; base fused to be clasping or perfoliate; adaxial and abaxial glabrous and matte; on stem to about 20 mm long and 18 mm across near middle, on rachis to about 8 mm long and 16 mm across, decreasing distally;

Stipule color: Between RHS 145B and RHS 145A both adaxial and abaxial;

Inflorescence: Terminal compound corymb; flowering to about 24 cm across and 18 cm tall;

Flower buds: Globose to obpyriform; glabrous, matt; about 4.5 mm diameter and 4.5 mm tall; color distal portion moderately blushed to solid between RHS 83C and RHS 86B, proximal and middle portion nearest RHS 145D;

Flower: Actinomorphic; semi-globose; to about 2 cm across and 1 cm tall;

Flower fragrance: Faintly sweet;

Blooming period: Late spring for about 4 weeks;

Lastingness of individual flower: About 5 days;

Flower quantity: About 200 to 500 per stem;

Flower aspect: Outwardly to upwardly;

Calyx: Cruciform; cupped; to about 4.5 mm across and 2 mm deep;

Tepals: Four; elliptic; obovate; concave; rounded apex; cuneate base; entire margin; 3 mm long and 2 mm wide;

Tepal color: Variable, adaxial nearest RHS 83C and nearest RHS NN155D, abaxial nearest RHS 83D and nearest RHS NN155D;

Peduncle: Terete; fistulous; glabrous; slightly glaucous; strong; stiff; heavily branched; about 92 cm long from lowest branch and 5 mm diameter; aspect upright; about 8 branches per peduncle at about 50° angle above horizontal; branches to about 70 cm long and 3 mm diameter decreasing distally;

Peduncle color: Nearest RHS 147B with strong blush to solid RHS 187A;

Pedicel: Cylindrical; glabrous; smooth; lustrous; to about 14 mm long and 0.5 mm diameter, average about 13 mm long and 0.5 mm in diameter; moderate in strength; aspect upwardly to outwardly;

Pedicel color: Nearest 146D proximally and nearest RHS 145C distally;

Gynoecium: About 10 pistils; superior; on stipe;

*Stipe*.—To about 2 mm long and 0.2 mm diameter; aspect upright; color nearest RHS 155A.

*Stigma*.—Oblong; to about 0.5 mm long and 0.3 mm across; color nearest RHS NN155A.

*Style*.—Cylindrical; short to about 0.2 mm long; color nearest RHS 155A.

*Ovary*.—Ellipsoidal with acute apex and base; glabrous; about 1 mm long and 0.5 mm across; color between RHS 182D and RHS 186C.

Androecium: About 60 stamens;

*Filaments*.—Cylindrical; lustrous; about 10 mm long and 0.5 mm wide near apex; color nearest RHS NN155D.

*Anthers*.—Oblong; to about 1 mm long and 0.5 mm across; color nearest RHS 18C.

*Pollen*.—Moderate quantity; color nearest 11B.

Fruit and seed: Not yet been observed;

Pest and disease resistance: Pest and disease resistance beyond what is typical of that of other Meadow Rue has not been observed.

Growth: The new plant is winter-hardy from USDA zones 5 to 8 and grows best with ample moisture, adequate drainage, and full sun.

I claim:

1. A new and distinct cultivar of *Thalictrum* plant named 'Cotton Ball' as herein described and illustrated.

* * * * *